United States Patent [19]
Allington

[11] Patent Number: 5,239,359
[45] Date of Patent: * Aug. 24, 1993

[54] ABSORBANCE MONITOR

[75] Inventor: Robert W. Allington, Lincoln, Nebr.

[73] Assignee: Isco, Inc., Lincoln, Nebr.

[*] Notice: The portion of the term of this patent subsequent to Aug. 20, 2002 has been disclaimed.

[21] Appl. No.: 909,251

[22] Filed: Sep. 19, 1986

Related U.S. Application Data

[60] Division of Ser. No. 833,518, Feb. 21, 1986, abandoned, which is a continuation of Ser. No. 351,193, Feb. 22, 1982, abandoned, which is a continuation-in-part of Ser. No. 44,763, Jun. 1, 1979, Pat. No. 4,536,091.

[51] Int. Cl.$^5$ .............................................. G01J 3/42
[52] U.S. Cl. ..................................... 356/319; 356/328
[58] Field of Search ............... 356/410, 411, 435, 319, 356/320, 328, 332, 334

[56] References Cited

U.S. PATENT DOCUMENTS

| | | | |
|---|---|---|---|
| 2,948,184 | 8/1960 | Johnson | 356/328 |
| 3,120,608 | 2/1964 | Bird | 356/246 |
| 3,591,801 | 7/1971 | Watson | 356/435 |
| 4,014,612 | 3/1977 | Atwood et al. | 356/435 |
| 4,030,828 | 6/1977 | Sonobe et al. | 356/320 |
| 4,076,420 | 2/1978 | De Maeyer et al. | 356/73 |
| 4,192,614 | 3/1980 | deMey, II et al. | 356/410 |
| 4,208,129 | 6/1980 | Spencer | 356/435 |
| 4,241,998 | 12/1980 | Farkas et al. | 356/319 |

OTHER PUBLICATIONS

Rudberg "Spectrophotometer with Linear Output" IBM Tech. Disc. Bulletin, vol. 20 #7, Dec. 1977 pp. 2767-2769.
Gilbert Jr. "Optimizing Monochromator Performance Electro-Opt Sys-Des(USA)" vol. 7 #2 Feb. 1975 pp. 25-31.
Jenkins et al "Fundamentals of Optics" Copyright 1957 McGraw-Hill pp. 137.

Primary Examiner—Vincent P. McGraw
Attorney, Agent, or Firm—Vincent L. Carney

[57] ABSTRACT

To reduce noise in an absorbance monitor in which the light source is a deuterium lamp, an aspheric condensing mirror focuses light from an approximately 0.6 mm-high by 2 mm-wide part of the central bright spot in the deuterium lamp through a slit in an aperture plate which blocks all other light and an aspheric monochromator mirror focuses the light onto a plane reflective diffraction grating, which: (1) is mounted for orbiting about an axis parallel to the longitudinal axis of the slit; and (2) adjusted so that, as it orbits it reflects a selected wavelength of light to a beam splitter. Each beam is focused upon and transmitted through a different one of two equal oval apertures optically at least as large as the height of the image of the aperture near the lamp. The beams are converted to an electrical signal by silicon diode photosensors, thus using only light: (1) focused in both transverse planes and originating from the same spot on the central bright spot; and (2) with the same relative geometric weighting for light propagating in various directions from various subparts of the central bright spot. To reduce noise originating from flow-related refraction effects in the flow cell, the flow cell has reflective walls and a large collecting mirror focuses light entry in a large cone from the flow cell into a measuring photocell. This large cone has a wider angle than the cone of light entering the flow cell.

1 Claim, 5 Drawing Sheets

ABSORBANCE MONITOR

REFERENCE TO RELATED APPLICATIONS

This application is a division of U.S. application Ser. No. 833,518, now abandoned, for ABSORBANCE MONITOR tiled by Robert William Allington on Feb. 21, 1986 which is a continuation of U.S. application Ser. No. 351,193, now abandoned, for ABSORBANCE MONITOR filed by Robert William Allington on Feb. 22, 1982 which is a continuation-in-part application of U.S. application Ser. No. 044,763 (now U.S. Pat. No. 4,536,091) for ABSORBANCE MONITOR filed by Robert William Allington on Jun. 1, 1979, and all are assigned to the same assignee as this application.

BACKGROUND OF THE INVENTION

This invention relates to light absorbance monitors.

In one class of light absorbance monitor, light from a gas tube discharge lamp is split into two beams. One of the beams of light is passed through an effluent to sense the absorbance of the effluent and the other is used as a reference beam.

After the sensing beam of light has passed through the effluent, both beams are converted to electrical signals. The electrical signals are compared to remove the indications relating to the reference values and common-mode noise, leaving a signal which is indicative of the absorbance or the transmittance of light. The signal is processed to obtain a visible indication of the effluent's light absorbance or light transmittance. This indication may be recorded or simply indicated on a meter.

In a prior art absorbance meter of this type, the light source is a low-pressure mercury vapor lamp. Noise is reduced from the light in this lamp prior to splitting the beam by passing it through an aperture which may or may not include a fluorescent screen.

This type of absorbance monitor has a disadvantage in that some noise remains which relates to fluctuations in common-mode light intensity. Moreover, the frequency selection of light from such sources is limited.

SUMMARY OF THE INVENTION

Accordingly, it is an object of the invention to provide a novel radiation monitor.

It is a further object of the invention to provide a novel light monitor for radiation having a gas discharge lamp as its light source.

It is a still further object of the invention to provide a novel absorbance monitor having low noise characteristics.

It is a still further object of the invention to provide a light source which eliminates noise in the light emitted in a beam.

It is a still further object of the invention to provide a novel gas discharge light source with low noise due to time variations in the intensity of light propagated in different angular directions from different sub-areas of the source.

It is a still further object of the invention to provide an inexpensive dual-beam light source which removes common-mode noise from the beams and the noise originating from time-varying angular and positional fluctuations in light intensity within the light source.

It is a still further object of the invention to provide a flow photometer which is relatively insensitive to flow-related light scattering within its flow cell.

It is s still further object of the invention to provide a sensitive, absorbance detecting flow photometer which has low flow-noise.

These problems have been reduced by the technique covered in the aforesaid related application which discloses a light absorbance monitor having a gas discharge light source, an optical detecting and electrical sensor station and a common-mode noise cancellation circuit. This light absorbance monitor includes in the gas discharge lamp light spot within the central bright spot of the gas discharge lamp onto a small aperture in an aperture plate which blocks all other light from the lamp. In one embodiment the intensity of the light is regulated by a feedback circuit from the common-mode noise cancellation circuit to reduce fluctuations.

The light which is passed through the small aperture in the light source is reflected by an aspheric focusing mirror onto a monochromator grating which selects the frequency of light to be applied to the sample being measured. The light from the monochromator is transmitted to a beam splitter, which splits the beam into two beams, one of which is to be used as a sensing beam for the transmittance or absorbance of the sample and the other of which is a reference beam. The beam splitter is of a type which provides as little plane polarization of the light as possible.

The sensing beam from the beam splitter is transmitted through a cell containing the sample, after having a certain portion of the image of the aperture near the light source focused through a small aperture which is part of the aperture stop of the sample cell, and onto a measuring photocell. Similarly, the reference beam is passed through an exactly similar aperture, which passes the same certain portion of the image of the aperture near the light source, onto a reference photocell. A reference cell containing a solvent or the like without the sample may also be interposed in that beam under some circumstances.

In the common-mode noise cancellation circuit, two electrical signals, one resulting from the sensing beam of light after passing through the sample in the optical detecting and electrical sensing station and the other being a reference electrical signal from the reference beam of light, are ratio-compared to remove almost all of the common-mode noise, the resulting signal being used as an indication of the absorbance or transmittance of the sample. Within the common-mode noise cancellation circuit is a circuit to generate the logs of the measurement and reference signals. The log reference signal output from this circuit is fed back to the lamp intensity control to reduce vestigial common-mode noise which is otherwise incompletely cancelled due to lack of ideal balance of the sample and reference signals.

It has been found that noise can be further reduced in the above arrangement by refinements which improve focusing of light while retaining a sufficient amount of flux obtained from the deuterium lamp so that photon quantum noise doesn't become too large. This is accomplished by utilizing two phenomena, which are: (1) the directional noise in the light increases as the distance to the center of the spot increases; and (2) as different frequencies of light are selected and foci of light in the two transverse planes change, there is a relationship between the change in the foci that permits selection of less noisy light because the noise varies with the frequency or wavelength of the light.

It has been discovered that if a slot is used extending in one direction and having a ratio of height to width selected so that its wider dimension increases the light flux and its narrower dimension removes the most noisy portion of unfocused light in one direction, better results are provided when the axis of the narrower dimension is adjusted for proper focusing so that light in the same focus as the adjusted focus is preferentially selected.

In accordance with this concept, light is obtained from a slot of a ratio of sides such as width to height of at least one-and-one-half to one. An aspheric condensing mirror focuses light from a similar area of the bright spot of the deuterium lamp through this slot and that light is focused by an aspheric focusing mirror onto a diffraction grating which orbits about a selected point to determine the angle that the light impinges upon it. The radius and path of orbit are selected so that, as frequencies are selected, the focus along one axis, which is the height axis in the preferred embodiment, is corrected. This axis is orthogonal to the longitudinal axis of the slot and is the dispersion axis of the grating.

The light is focused through a reference cell and a flow cell where it is to be measured through apertures whose maximum width is no larger than the slot to produce corresponding spots which are corrected in both the tangential (height) axis and the sagittal (longitudinal) axis for changes in focus to emphasize only the least noisy light. The apertures may, for example, be circular cross-section apertures one millimeter in diameter and the corresponding spot may be ¾ millimeter high by one and one-half millimeters wide. The tangential axis is kept in focus by the orbiting of the grating and the Saggital axis is less well focused, but focused as well as possible by the aspheric nature of the focusing mirror.

The flow cells include means for reducing noise associated with flow-related refraction effects in the flow cell. It is known from U.S. Pat. No. 4,276,475 granted Jun. 30, 1981 to Kenneth E. Nelson for a novel photometric system to reduce these effects by using a cone-shaped flow cell. The use of cone-shaped flow cells in the manner of this patent increases the volume of the light path, thus degrading the resolution.

To reduce noise associated with flow-related refraction effects such as Schlieren scattering without unnecessarily increasing the volume of the light path, the walls of the flow cell are coated with a reflective coat without tapering the walls of the flow cell to cause its size to increase as its distance from the light source increases and without blocking light light from the entrance in a manner that prevents the light entering the flow cell to be transmitted through the entire volume and be collected to generate a useful signal.

The light exiting the measuring flow cell has somewhat more angular dispersion than light entering because of Schlieren scattering due to temperature gradients and motion of the flow cell contents. All this light must be collected onto the measuring flow cell or the noise cancellation will be compromised. Further, if all the Schlieren scattered light does not reach the measuring photocell, new and additional noise associated with the flow of liquid within the flow cell will result. The reflective flow cell walls accomplish this. Coated, constant-diameter walls have been used before but not in this combination where special unexpected benefits result. The light is then received by silicon diodes or other devices, the sensitiving of which is uniform across their entire area.

Since a large photocell would introduce further noise for electronic reasons, an aspheric collection mirror focuses all of the light exiting the measuring cell into a small area entirely within the sensitive area of a fairly small measuring photocell. The measuring photocell is thus large enough not to constitute another aperture stop after the flow cell. Only the light-entrance side of the flow cell constitutes a measuring path aperature stop since its walls are smooth and highly reflective. The sensitive area of the reference photocell constitutes an aperture stop in the reference path.

From the above description, it can be understood that the light absorbance monitor of this invention has several advantages such as: (1) it is economical and simple in construction; (2) it removes substantially all noise from the light source inexpensively except common-mode noise; and (3) it removes the common-mode noise electrically in an advantageous manner.

SUMMARY OF THE DRAWINGS

The above noted and other features of the invention will be better understood from the following detailed description when considered with reference to the accompanying drawings in which.

DETAILED DESCRIPTION

Figure 1:
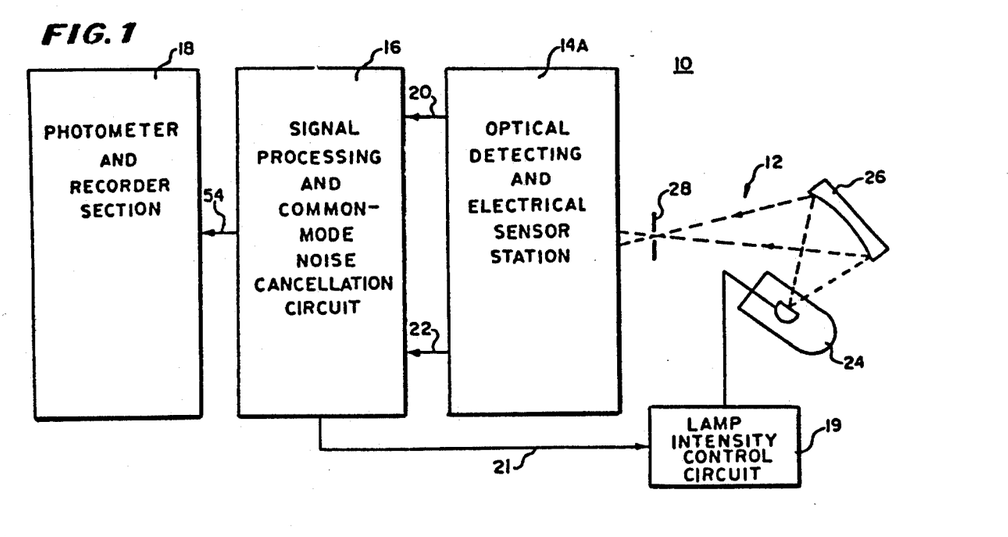
FIG. 1 is a block diagram of an absorbance monitor having a light source in accordance with an embodiment of the invention.

In FIG. 1, there is shown a block diagram of a light absorbance monitor 10 having a light source 12A, an optical detecting and electrical sensor station 14A, a signal-processing and common-mode noise cancellation circuit 16, a photometer and recorder section 18 and a lamp intensity control circuit 10. These units are similar to the corresponding parts of the absorbance monitor described in the related application U.S. application Ser. No. 044,763 for ABSORBANCE MONITOR filed by Robert William Allington on Jun. 1, 1979 (now U.S. Pat. No. 4,536,091) except for certain differences between the light source 12A and optical detecting and electrical sensor section 14A of this invention and the corresponding parts 12 and 14 of the aforesaid application.

The light source 12A generates a beam of light which has noise present in it due to fluctuations originating in the gas discharge lamp and transmits that beam of light to the optical detecting and electrial sensor station 14A. The optical detecting and electrical sensor station 14A splits the beam of light and senses an effluent concentration and the lamp noise with one beam, designated the measuring beam, using the other beam as a reference beam which senses lamp noise alone. The light is detected by a sensor and electrical signals are transmitted through conductors 20 and 22 to the signal-processing and common-mode noise cancellation circuit 16. These electrical signals carry information about the effluent or other material sensed in the optical detecting and electrical sensor station 14A by the beam of light from the light source 12A.

The signal-processing and common-mode noise cancellation circuit 16 removes the common-mode noise and performs other routine processing on the signal before transmitting it to the photometer and recorder section 18 which records or indicates the information and therefore the material through which it has been passed for monitoring of absorbance. The lamp intensity control circuit 19 is electrically connected to the cathode of deuterium lamp 24 and controls the power applied to the lamp to thus regulate the lamp and reduce fluctuations in intensity. It is controlled by feedback from the signal-processing and common-mode noise cancellation circuit 16 through a conductor 21.

To provide a beam of light to the optical detecting and electrical sensor station 14A, the light source 12A includes a deuterium lamp 24, a mirror 26 and an aperture plate 28. The mirror 26 is an aspheric condensing mirror positioned to focus the image of a small portion of the source of the deuterium lamp 24 onto a small aperture in the aperture plate 28, which is positioned between the deuterium lamp 24 and the optical detecting and electrical sensor station 14A. Advantageously, the small portion of the source is a portion of the central bright spot and this portion of the central bright spot is focused on the aperture, which is approximately 0.6 mm high by 2 mm wide (direction perpendicular to the paper).

Light from portions of the deuterium lamp 24 that is not focused through the aperture in aperture plate 28 may have intensities of light transmitted in different directions which vary with respect to each other. Such light is either not received by the mirror or reflected in directions which are not focused directly on the aperture in the aperture plate 28 so that a high intensity light from a single small spot in the central bright spot of the deuterium lamp 24 is focused on the aperture in the aperture plate 28, all other light being blocked from the optical detecting and electrical sensor station 14A by the plate.

While an aspheric condensing mirror 26 is shown, it is obvious that a lens or groups of lenses and mirrors may be used. The feature that is significant is that the light from a single spot in the deuterium lamp 24 is focused directly on the aperture in the aperture plate 28 to provide a strong beam of light from one spot which dominates the light passing through the aperture plate 28 to the optical detecting and electrical sensor station 14A.

This light may include common-mode noise due to variation of the light at the one point which is focused on the aperture in the aperture plate 28 but light fluctuations in the intensity of light in one direction with respect to the intensity in another direction does not affect the ratios of intensities of the beams being passed to the optical detecting and electrical sensor station 14A. The ratios of intensities of the beams are not affected because only light from one spot passes the aperture plates 28 with any significant intensity and light from all directions and all areas in the source are equally weighted in the ratio measurements made by station 14A and circuit 16.

Figure 2:
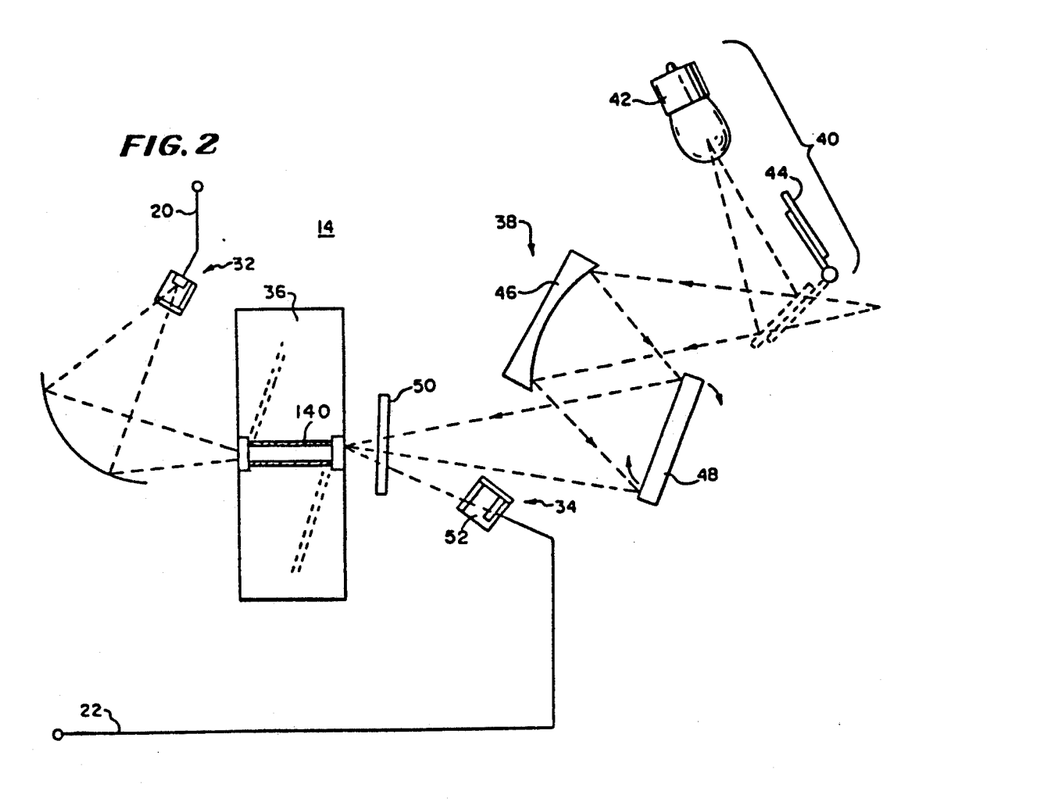
FIG. 2 is a schematic diagram of a portion of the embodiment of FIG. 1.

In FIG. 2, there is shown a schematic diagram of the optical detecting and electrical sensor station 14A having measuring and reference photocells 32A and 34A respectively, a flow cell 36 and monochromatic optical system 38.

The optical system 38 receives light from the light source 12A (FIG. 1) and processes the beam to select a specific frequency, after which it splits the beam into two beams, one of which is applied through the flow cell 36 and onto the measuring photocell 32 and the other of which is applied to the reference photocell 34. A second reference flow cell or reference sample may be positioned in the beam that is applied to the reference photocell 34A although one is not shown in FIG. 2. The optical detecting and electrical sensor station 14A also includes an incandescent lamp section 40 having a tungsten-krypton lamp 42 and a pivotable flat mirror 44.

The optical system 38 includes an aspheric monochromator focusing mirror 46, a diffraction grating assembly 48 and a beam splitter 50. The aspheric monochromator focusing mirror 46 is positioned to receive the light from the light source 12A (FIG. 1) and focus it upon the diffraction grating assembly 48.

The diffraction grating assembly 48 serves as a monochromator and includes a reflective diffraction grating which may be pivoted to change the frequency of light it selects. The beam splitter 50 is positioned between the reflected light from the diffraction grating assembly 48 and the light path entrance at the right side of the flow cell 36 to permit light to pass from the diffraction grating assembly 48 and be focused upon the light path entrance, and to focus another beam downwardly.

The reference photocell is at the focus of the second beam formed by the beam splitter 50 so that one beam of light passes through the flow cell and on to the measuring photocell 32A and the other beam of light impinges upon the reference photocell 34 and is identically focused upon the sensitive area of the reference photocell which is the same size and shape as the entrance of the light path.

In the preferred embodiment the beam splitter 50 is a quartz plate positioned to split the beam without polarizing the light. For this purpose it is positioned at an angle sufficiently close to being normal to the incident light to make the amount of plane polarization negligible of the light but yet at a sufficient angle to provide beam splitting with a reflection of light to the reference photocell 34. It is desirable to prevent plane polarization because it has been found that such polarization increases noise and apparently light from the light source varies in intensity along different axes of polarization.

A ten degree deviation from normal to provide reflected light twenty degrees from the incident light has been found to be suitable for the quartz plate and to be sufficiently far from the Brewster angle so that the component of plane-polarized light is negligible. Of course, any other technique for providing two beams of light from the one beam of light without significant polarization is suitable.

The flow cell 36 includes an inherent aperture stop at its one-millimeter diameter circular or oval light-path entrance of the same size and shape as the sensitive area of the reference photocell 34. Thus the sensitive area of the reference photocell 34 serves as an aperture and does not require a separate aperture plate. The locations of the flow cell entrance aperture stop and the photocell aperture stop are such that the same portions of the image of light passing through the aperture plate 28 (FIG. 1) may be focused within the aperture stop in the flow cell 36 and the aperture stop in the photocell 34. Certain of this light from the flow cell 36 is collected by the collecting mirror 126 and focused onto the measuring photocell 32 in a manner to be described hereinafter.

In the preferred embodiment, the optical system between aperture plates provides magnification of 1.3 times. The aperture stop in the photocell 34 and the aperture stop provided by the light path entrance of the flow cell 36 is one millimeter in diameter so that the image of the aperture in the plate 28 (FIG. 1), which is 0.6 mm high by 2 mm wide, is commensurate in height with them.

the pivotable flat mirror 44 in the incandescent lamp section 40 may be pivoted to an upward position to permit light from the light source 12A (FIG. 1) to pass or may be pivoted downwardly to block that light and instead reflect light from the tungsten-krypton lamp 42 to the aspheric monochromatic focusing mirror 46. This alternate source of light is compatible with the embodiment shown since the lamp has a slit-shaped filament.

The conductor 20 is electrically connected to the measuring photocell 32 to provide an electrical signal which is representative of the light absorbance by the material in the flow cell 36 and the conductor 22 is electrically connected to the photocell 20 to provide a reference signal which is equivalent to the light. These signals are connected to the signal-processing and common-mode noise cancellation circuit 16 (FIG. 1).

Figure 3:
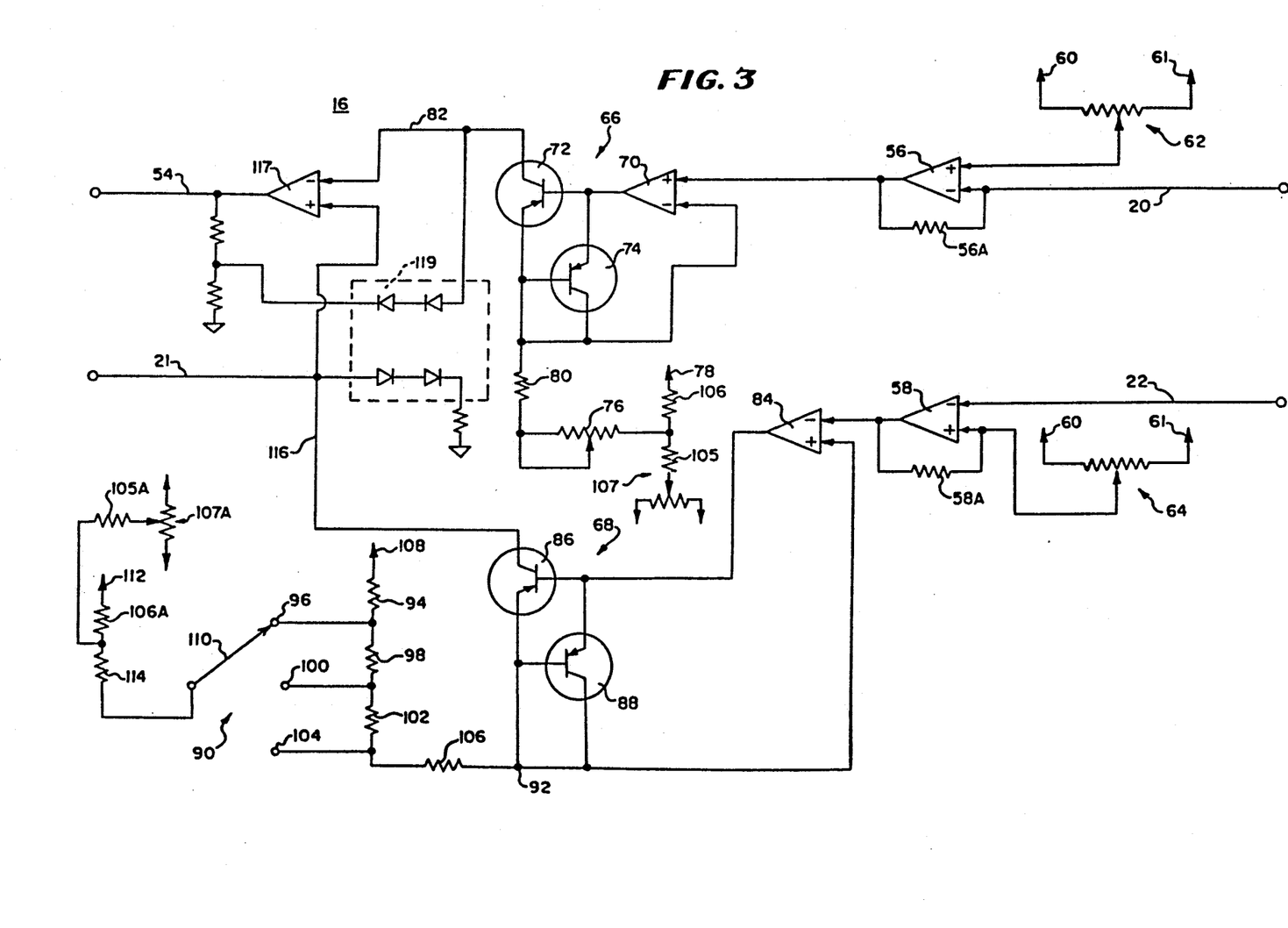
FIG. 3 is a schematic circuit diagram of still another portion of the embodiment of FIG. 1.

In FIG. 3, there is shown a schematic circuit diagram of the signal-processing and common-mode noise cancellation circuit 16 for (1) receiving the measuring electrical signals on conductor 20 and the reference signal on conductor 22; (2) cancelling noise; and (3) applying an output signal to the photometer and recorder section 18 (FIG. 1) through a conductor 54. The photometer and recorder section 18 plays no part in this invention except to receive the signal and otherwise may operate in the manner of any photometer and recorder section of an absorbance monitor.

The photocurrents from the measuring and reference photodetectors are led respectively to the inverting inputs of differential amplifiers 56 and 58. Feedback resistors 56A and 56B determine the gain of the simplifiers.

To correct the signals on conductors 20 and 22 for dark current from the photocells, the signal-processing and common-mode noise cancellation circuit 16 includes means for subtractive cancellation of the amplifier offset potentials.

To provide a signal for subtraction from the signals on conductors 20 and 22, the differential simplifier 56 has its positive or noninverting input electrically connected to a source of adjustable potential through an adjustable potentiometer 62 leading to a pair of sources of fixed potentials generally indicated at 60 and 61. The differential amplifier 58 has its positive noninverting input terminal electrically connected to the source of adjustable potential through a similar adjustable potentiometer 64. The negative or inverting input terminal of differential amplifier 56 is electrically connected to conductor 20 and the negative or inverting input of differential amplifier 58 is electrically connected to the conductor 22.

To adjust the baseline and convert the voltage signal to a current signal, the signal-processing and common-mode noise cancellation circuit 16 includes a fine baseline adjust circuit 66 and a coarse baseline adjust circuit 68, each of which have incorporated in them a different voltage-to-current converter.

The fine baseline adjust circuit 66 includes a differential amplifier 70, a first PNP transistor 72, a second PNP transistor 74 and an adjustment potentiometer 76. The output of differential amplifier 56 is electrically connected to the positive input of differential amplifier 70.

To provide voltage-to-current conversion of the signal: (1) the base of PNP transistor 72 and the emitter of PNP transistor 74 are electrically connected to the output of differential amplifier 70; and (2) the collector of PNP transistor 74, the base of PNP transistor 74, and the emitter of PNP transistor 72 are electrically connected to the inverting or negative input terminal of differential amplifier 70.

To provide fine adjustment of the baseline, a 15 volt source of positive potential 78 is connected through resistor 106, the adjustment potentiometer 76 and a fixed resistor 80 and the negative input terminal of the differential amplifier 70 in series in the order named. The incoming signal to differential amplifier 70 is reduced by the signal to the negative input terminal of differential amplifier 70 which is adjusted by the adjustment potentiometer 76 to adjust the baseline. Adjustment of potentiometer 76 varies the emitter (and collector) current of PNP transistor 72 in response to a given input voltage at the positive input terminal of differential amplifier 70, thus adjusting the baseline.

The coarse baseline adjust circuit 68 includes the differential amplifier 84, a first PNP transistor 86, a second PNP transistor 88, and a coarse baseline correction switch circuit 90. The positive or noninverting terminal of differential amplifier 84 is electrically connected to the output of differential amplifier 58.

To provide voltage-to-current conversion of the signal: (1) the output of differential amplifier 84 is electrically connected to the base of PNP transistor 86 and to the emitter of PNP transistor 88; and (2) the emitter of PNP transistor 86, the base of PNP transistor 88 and the collector of PNP transistor 88 are each electrcally connected to a terminal 92 of the coarse baseline correction switch circuit 90.

To provide coarse adjustment of the baseline, the stator for the coarse baseline correction switch circuit 90 includes a first resistor 94, a switch contact 96, a second resistor 98, a second switch contact 100, a third resistor 102, a third switch contact 104, and a fourth resistor 106 electrically connected in series in the order named between a source of positive potential 108 and the terminal 92. The armature includes a switch arm 110 adapted to selectively connect the first, second or third switch contacts 98, 100 or 104 respectively. While four resistors and three switch contacts are shown and described, in the actual embodiment there are more fixed switch contacts and more resistors in the switch to provide greater adjustment flexibility.

To adjust the amplitude of the signals to be subtracted to compensate for dark current, a first adjustment circuit includes: (1) a first potentiometer 107; (2) a source of ground potential connected to one side of the potentiometer 107; (3) a source of positive 30 volts connected to the other side of the potentiometer; and (4) a resistor 105 having one end connected to the adjustable top of the potentiometer 107, and its other end connected to the resistor 76 and the cource of potential 78 through resistor 106. A second adjustment circuit includes: (1) a second potentiometer 107A; (2) a source of ground potential connected to one side of the potentiometer 107A; (3) a source of positive 30 volts connected to the other side of the potentiometer; and (4) a resistor 105A having one end connected to the adjustable top of the potentiometer 107A, and its other end connected to the resistor 76 and the source of potential 112 through a resistor 106A and to switch 110 through a resistor 114.

The switch arm or armature 110 of the coarse baseline correction switch circuit 90 is electrically connected to the source of positive potential 112 through the resistor 114 and resistor 106A to provice a variable resistance in series with the positive potential 108 to the differential amplifier 84 for coarse baseline correction. The collector of PNP transistor 86 provides the corrected reference current signal on a conductor 116. To convert the signals to logarithmic so as to represent absorbance, a matched diode log conversion circuit 119 is electrically connected to conductors 116 and 82 and conductor 116 is connected to conductor 21 to control the intensity of the deuterium lamp 24 (FIG. 1). This circuit may be of the type described in U.S. Pat. No. 3,676,686 issued to Robert W. Allington to HIGH SENSITIVITY LIGHT ABSORBANCE APPARATUS on Jul. 11, 1972. It is advantageous to use series-connected diodes in that circuit.

To eliminate common-mode noise, the signal-processing and common-mode noise cancellation circuit 16 includes a differential amplifier 117 having its inverting or negative terminal electrically connected to the conductor 82 and its positive or noninverting terminal electrically connected to the conductor 116. The output of the differential amplifier 117 is also electrically connected to the conductor 54.

Conductor 54 receives the electrical sensing signal after correction by subtraction or cancellation of the reference signal, baseline errors and the dark current of the photocells, thus providing a signal to the photometer and recorder section 18 (FIG. 1) indicative of the absorbance of light in the flow cell. In this process, the common-mode noise coming from the gas discharge lamp is cancelled within the differential amplifier 117 between the reference signal and the measured signal.

Before operating the light absorbance monitor 10 (FIG. 1) to detect the light absorbance of the components of a sample, certain adjustments are made. One such adjustment is the cancelling of dark current in the photocells 32 and 34. To accomplish this, the lamps are extinguished and the adjustable potentiometers 62 and 64 (FIG. 3) adjusted while the outputs from the differential amplifier 56 and 58, or from each pair of the log diodes shown in FIG. 4 of U.S. Pat. No. 3,676,686 are measured until the dark currents have been cancelled within the differential amplifiers 56 and 58.

In operation, with the pivotable flat mirror 44 in the position shown in FIG. 2, the deuterium lamp 24 in the light source 12A (FIG. 1) is the source of illumination for the optical system 38 (FIG. 2) and the photocells 32 and 34. The light radiated from the lamp fluctuates in intensity in two modes which are: (1) the arc within the deuterium lamp fluctuates in intensity position; and (2) the light is emitted with different fluctuating intensity from different parts of the lamp and the emitted light intensity in one direction fluctuates with respect to the intensity of light in another direction.

To prevent fluctuations in the intensity of light in the reference beam with respect to the sensing beam due to directional fluctuations in the lamp, the aspheric condensing mirror 26 is positioned such that the image of a small area covering a portion of the central bright spot in the arc is focused on the aperture of the aperture plate 28. With this arrangement, only a small portion of the arc passes substantial light intensity through the aperture plate 28. This light intensity fluctuates with the fluctuation of the single point in the arc within the deuterium lamp but there is no light transmitted with dissimilar fluctuations in intensity in different directions transmitted through the aperture plate 28 to the optical detecting and electrical sensor station 14A.

The light entering the optical detecting and electrical sensor station, as best shown in FIG. 2, is focused by the aspheric monochromator focusing mirror 46 onto the diffraction grating assembly 48. The diffraction grating in that assembly is adjusted to reflect a selected frequency of light to the beam splitter 50 and through the windows of the flow cell 36 onto the measuring photocell 32.

The beam splitter 50 splits the beam of light, without significant polarization of it, and focuses a portion of it through the aperture plate 52 onto the reference photocell 34. The aperture stop in the flow cell 36 in front of the photocell forms an aperture for the light equivalent in size to the aperture in the aperture plate before the reference photocell, each being just large enough to receive within them the entire image of the aperture in the aperture plate of the light source. The measuring photocell 32 generates an electrical signal from the light passing through the flow cell 36 and applies it to conductor 20 and the reference photocell 34 generates an electrical signal and a response to the light impinging upon it and applies it to the conductor 22.

Before the material which is to be studied in the absorbance monitor flows through the flow cell but usually after a solvent which is to carry the material has been applied, the baseline is adjusted. This is accomplished by switching the switch arm 110 of the coarse baseline correction stepping switch circuit 90 (FIG. 3) until the baseline is fairly close to the desired level. The fine adjustment potentiometer 76 is then also adjusted. These adjustments may be made periodically during measurements to reduce baseline offset and increase the usable amplitude of the signal.

When the equipment is ready for a measurement, the effluent to be measured is permitted or caused to flow through the flow cell 36. The signal on conductor 20 now is altered in accordance with the absorbance of light by the effluent and by the solvent carrying the effluent whereas the conductor 22 carries a signal which is affected only by the solvent. Both signals may have common-mode noise originating from the light source 12A(FIG. 1).

To remove the common-mode noise, the signals on conductors 20 and 22, after they have passed through the differential amplifiers 56 and 58 respectively which remove the dark current from the photosensors where applicable and through the fine baseline adjust circuit 66 and the coarse baseline adjust circuit 68 which adjust for baseline, are applied to the differential amplifier 117. There the signals are subtracted from each other which produces and isolates the signal caused by the effluent and at the same time removes the common-mode noise produced in the lump 24(FIG. 1). Prior to subtraction in the differential amplifier, the signals are converted to the log of the signals in amplitude, using log converters. Feedback from the log converter controls the intensity of the light source.

This final signal is applied to conductor 54. It may be processed in ways known in the art in the photometer and recorder section 18 to provide indications of absorbance or transmittance of the effluent in the flow cell 36. Such processing is not part of this invention nor is the indicating on the detector or the recording since these are all well known in the prior art.

Figure 4:
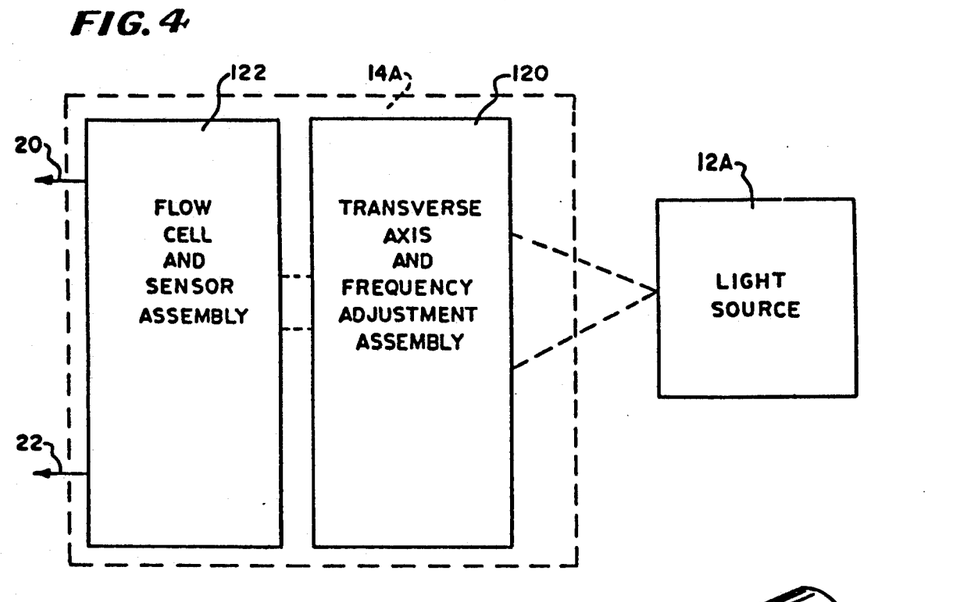
FIG. 4 is a block diagram of a portion of the invention of FIG. 1 illustrating a second embodiment.

In FIG. 4, there is shown a block diagram of an embodiment of light source 12A and optical detecting and electrical sensor station 14A similar to the light source 12 and optical detecting and electrical sensor station 14 of the aforementioned earlier case U.S. application Ser. No. 044,763 for ABSORBANCE MONITOR but adapted to have still better noise characteristics. The superior noise characteristics relate to the ability to focus light from a low-noise portion of a gas discharge lamp within the light source 12A.

In a manner analogous to the operation of the embodiment of the aforementioned application, the light source 12A provides a beam of light to the optical detecting and electrical sensor station 14A, which splits the beam of light into a sensing beam and a reference beam and senses characteristics of a sample and converts them to electrical signals. The electrical signals are transmitted through conductors 20 and 22 to the signal-processing and common-mode noise cancellation circuit 16 (FIG. 1). As in the embodiment of the aforementioned application, these electrical signals carry information about the effluent or other material sensed in the optical detecting and electrical sensor station 14A by the beam of light from the light source 12A.

To remove further noise associated with focusing, the optical detecting and electrical sensor station 14A includes: (1) a transverse axis and frequency adjustment assembly 120 (FIGS. 4, 6, 7 and 8); and (2) a flow cell and sensor assembly 122. The transverse axis and frequency adjustment assembly 120 is adapted to receive a beam of light from the light source 12A and to adjust its frequency. After adjusting the light's frequency, it is focused onto the flow cells and sensors of the flow cell and sensor assembly 122 for each difference frequency.

To focus only that light of the selected frequency that is from a low-noise portion of the lamp into the flow cell and sensors, the transverse axis and frequency adjustment assembly 120 directly focuses the light waves aligned substantially in the direction of the wavelength dispersion (substantially parallel to a first plane) to preserve its image information and is arranged to permit focused light waives substantially parallel to a second plane transverse to that first plane sagittal to pass to the flow cell and sensor assembly 122 while blocking unfocused light. Thus, focused light is preferentially utilized and unfocused light is discriminated against. The flow cell and sensor assembly 122 is adapted for maximum use of the light in a uniform manner to be described hereinafter. The discussion of the alignment of the waves herein refers to the electric field component of the electromagnetic light radiation.

Figure 5:
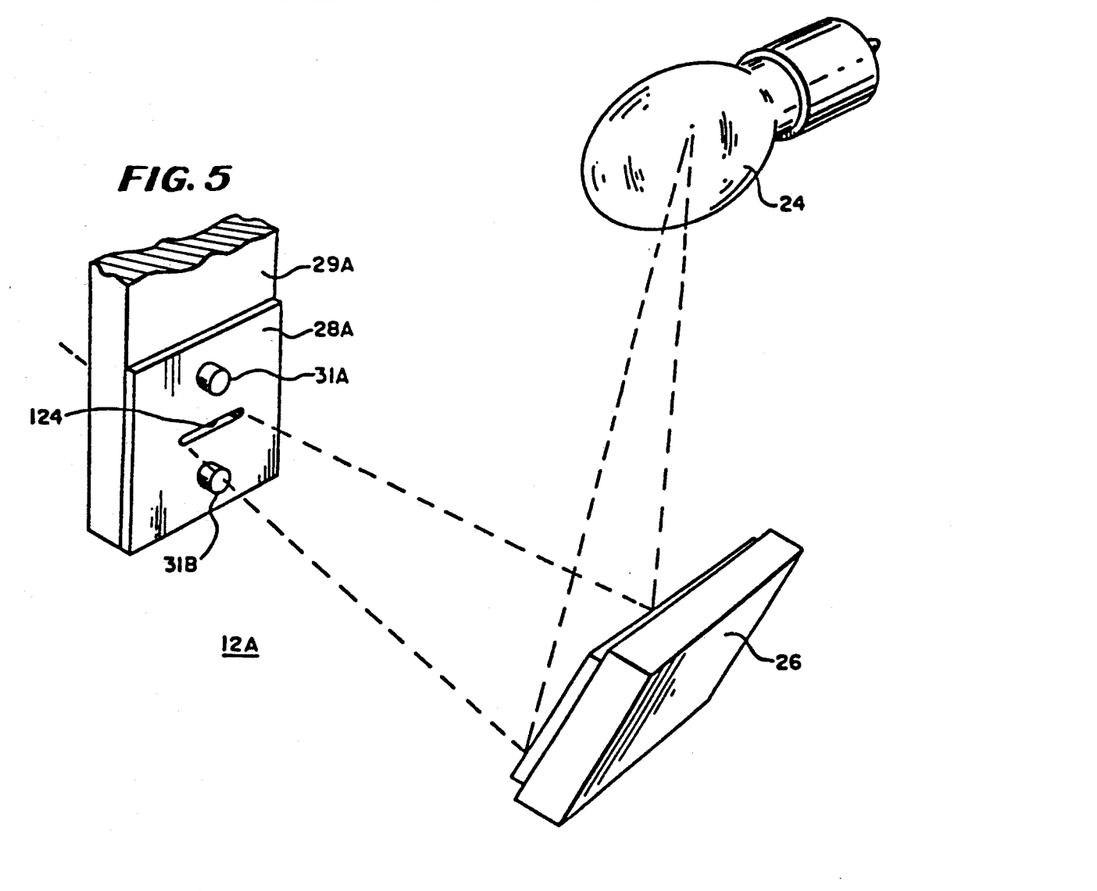
FIG. 5 is a simplified perspective view of a portion of the embodiment of FIG. 4.

In FIG. 5, there is shown a simplified perspective view of the light source 12A having a deuterium lamp 24, an aspheric condensing mirror 26 and an aperture plate 28A. The aspheric condensing mirror 26 is positioned to focus light from a portion of the central bright spot of the deuterium lamp 24 onto a slot in the aperture plate 28A.

The aperture plate 28A differs from the aperture plate 28 in the embodiment of FIG. 1 in that it includes a slot 124 instead of the circular aperture included in the aperture plate 28 in the embodiment of FIG. 1. The slot 124 in the preferred embodiment is 0.6 mm (millimeters) wide and two millimeters long. The aspheric condensing mirror 26 focuses light from a similar size and shape area at the central bright spot of the deuterium lamp 24 through the slot 124, with other more noisy light being blocked by the aperture plate.

The slot 124 has a longitudinal axis in the direction of its two millimeter dimension and this passes through the image of the center of the bright spot of the deuterium lamp 24 which is centered upon it. Directly in the center of the slot 124 there is virtually no noise, but the noise increases as the distance from the center increases. The aperture plate is adjustably mounted to a frame 29A by two fasteners 31A and 31B. The light passing through the slot 124 is transmitted to the optical detecting and electrical sensor station 14A (FIG. 4) for use and the remainder of the light is blocked.

Figure 6:
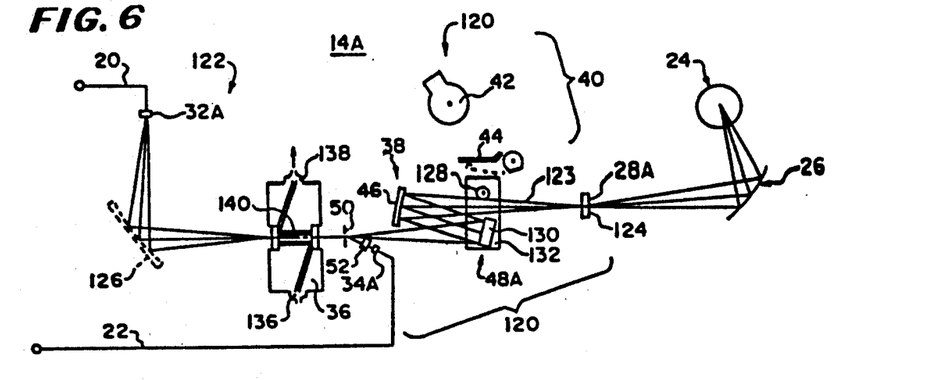
FIG. 6 is a simplified schematic view illustrating the operation of the embodiment of FIG. 4.

In FIG. 6, there is shown a schematic diagram of the optical detecting and electrical sensor station 14A having the transverse axis and frequency adjustment assembly 120 and the flow cell and sensor assembly 122, with with transverse axis and frequency adjustment assembly 120 being positioned with the pivotable flat mirror 44 raised as discussed above in connection with the embodiment of FIG. 1 so that light shown at 123 from the aperture plate 28A (FIG. 5) passes into the transverse axis and frequency adjustment assembly 120. The light entering this assembly is received by the aspheric monochromator focusing mirror 46 and focused onto the diffraction grating assembly 48A.

The light shown at 123 entering the optical detecting and electrical sensor station 14A diverges as it moves from the slit to the aspheric monochromator focusing mirror 46 and, when reflected, converges onto the diffraction grating assembly 48A. The diffraction grating assembly 48A reflects the light to the beam splitter 50 which transmits one beam through the aperture stop formed by the entrance aperture of flow cell 36 and the other beam to the similarly sized aperture stop formed by the reference photosensor 34A.

The aspheric nature of the focusing mirror 46 corrects for the astigmatism inherent in the use of a plain grating with converging light, as well as the correction required by the off-axis focusing of the mirror. The surface of the mirror is shaped to correct for astigmatism origination in the grating as well as in the mirror itself, by measuring or calculating the astigmatism in each in a manner known in the art or obtaining it from the manufacturer and custom-shaping the mirror by trial and error or by trial calculations made repeatedly until it is corrected. It may also be corrected by trial and error in a set to be used together until there is no astigmatism in the combined grating and mirror. Standards are established for models of gratings and mirrors based on these trial-and-error techniques to reduce cost for production.

After passing through the flow cell 36, the light is reflected by an aspheric collecting mirror 126 onto the measuring photosensor 32A. Signals obtained by the reference photosensor 34A and measuring photosensor 32A are applied to the conductors 20 and 22 just as in the embodiment of FIG. 1.

The diffraction grating assembly 48A includes a pivot point 128, a plane reflective diffraction grating 130 and a diffraction grating lever arm 132. The diffraction grating lever arm 132 pivots about the pivot point 128 and carries the plane reflective diffraction grating 130 with it. The plane reflective diffraction grating 130 is mounted at an angle to the longitudinal axis of the diffraction grating lever arm 132.

The diffraction grating lever arm 132 is positioned by a mechanism (not shown in FIG. 6) for adjusting the angle of rotation of the diffraction grating lever arm 132 and thus the point in its orbit of rotation of the plane reflective diffraction grating 130. This point in the orbit is selected so that light from the aspheric monochromator focusing mirror 46 impinges upon the grating at a different angle for different orbital positions, causing a different frequency of light to be reflected at different points and at different angles from the grating.

The distance of the grating from the pivot point 128 and the angle of the grating are selected so that the waves aligned with the longitudinal axis of the slot 124 (FIG. 5) for each different frequency of light are reflected from the plane reflective diffraction grating 130 in focus with the beam splitter 50. The trajectory taken by the grating is chosen to maintain a constant location of the tangential focus at flow cell and reference photocell.

The image of light from the deuterium lamp (FIG. 5) is that of an elongated slot having its longitudinal axis parallel to the axis of the pivot point 128 and this image is focused onto the reference photocell and flow cell entrance aperture after reflection from the grating and reflection from a transmission through the beam splitter 50. Because it is elongated, only a portion of the light at a particular wavelength along the longitudinal axis is used whereas all the light along its shorter axis is used at a selected point along the longitudinal axis. The point along the longitudinal axis is selected automatically because there is a relationship between the point of focus on the two transverse axes of the deuterium lamp, one of which is tranverse to the slot and the other of which is parallel with the slot.

The focus of the light waves aligned with planes parallel to the slot and those transverse are related in their shifts in focus as the grating is moved so that, when the focus with respect to the axis transverse to the slot is positioned through the beam splitter 50 by the orbital location of the plane reflective diffraction grating 130 on the lever arm diffraction grating 132, the axis of the waves which are parallel to the slot are moved longitudinally along the slot and those that are properly focused at a particular point are transmitted through the beam splitter 50. Thus, light is transmitted to the beam splitter 50 which is focused at the point for waves parallel to the slot and perpendicular to the slot.

The beam splitter 50 in the embodiment of FIG. 6 operates in the same manner as the beam splitter 50 in the embodiment of FIG. 1 to reflect one beam of light through an aperture plate 52 onto a reference photosensor 34A and to transmit another beam through the flow cell. As in the embodiment of FIG. 1, the apertures are selected to have light from the same area of the deuterium lamp 24 (FIG. 5) transmitted to the reference photosensor 34A and measuring photosensor 32A.

It has been discovered that the photoelectron emissive surfaces of ordinary vacuum photoemissive photocells are nonuniform so that noise in the light beams is aggravated by variation in quantum efficiency of the photocathode from one location to another on its surface that receives light flux. This noise is not corrected by calibration because it changes with location of the noise in the beam. In the embodiment of FIG. 6, the reference photosensor 34A and measuring photosensor 32A are silicon diode photosensors, which have a uniform photosensitive surface so that, when the aperture stops are adjusted to coincide, the reference photocell and the entrance aperture in the flow cell 36 are adjusted with respect to each other, there is a noticeable reduction in noise in the signal.

In the embodiment of the aforementioned earlier application, the adjustment of the aperture plates was less effective for additional reasons, which are: (1) that common-mode noise in the beams affected the photosensors differently because sensitivity of the surfaces of the photosensors were not uniform; and (2) adjustment of the aperture plates was difficult because shifts of the position of the photosensors' surfaces receiving light and the lack of uniformity in the sensitivity of the surface caused unpredictable changes.

The flow cell 36 is similar to a prior art type of flow cell. It includes a flow path for the liquid to be measured with an entrance at 136 and an exit at 138. The fluid flows upwardly to a horizontal sleeve 140 with viewing windows on each end through which the light beam from the beam splitter 50 is transmutted.

The light passes through this horizontal sleeve 140 to the aspheric collecting (photocell focusing) mirror 126 and from there to the measuring photosensor 32A upon which it is focused. The horizontal sleeve 140 has reflective walls coated with Hastelloy C or other tarnish-free reflective material.

In a prior art embodiment using cadmium sulfide photocells to sense light passing through flow cells, the flow cell walls were coated to conserve light so that the cadmium sulfide photocells would receive enough light to provide adequate response speed. This type of prior art flow cell has shown special advantages in combination with silicon diode photocells or other sensors having uniform surface sensitivity but requiring sufficient light to exceed its noise threshhold as in the embodiment of FIGS. 2, and 4 because it passes off-axis light to the measuring photocell receives all of the light that the reference photocell receives. This is necessary to cancel all of the noise originating from the gas discharge light source. It also decreases noise associated with liquid flow within flow cell.

Temperature differences between various instantaneous locations in the flowing liquid within the light path of the flow cell form time-varying refractive index gradients. These gradients randomly refract light from its normal path that otherwise would be predicted by geometrical optics. This process is called "Schlieren scattering" and produces noise in the resulting measured absorbance reading. This "flow noise" is manifested as a larger noise level in the absorbance signal when the liquid stream is moving that that observed when the liquid is stationary or when the flow cell is dry.

It has been found that a flow cell with reflective walls reduces flow noise if its walls are very reflective and well-polished and care is taken to ensure that all of the light leaving the flow cell reaches the uniformly sensitive surface of the measuring photocell in spite of the reflected light being additionally diverged by Schlieren scattering.

It has been found that compressing the reflecting tube to an oval cross section to more nearly conform to a monochromatic image of the source aperture in aperture plate 28A (FIG. 5) or of the filament in the tungsten-krypton lamp improves the bandwidth-to-energy efficiency ratio by maximizing the energy-to-bandwidth efficiency ration. It may be desirable to match the shape of the sensitive area of the reference photosensor 34A (FIGS. 2, 6 and 8) to the oval shaped reflecting tube and image to decrease noise or to use an oval shaped mask in front of a larger photocell.

Figures 7, 10:
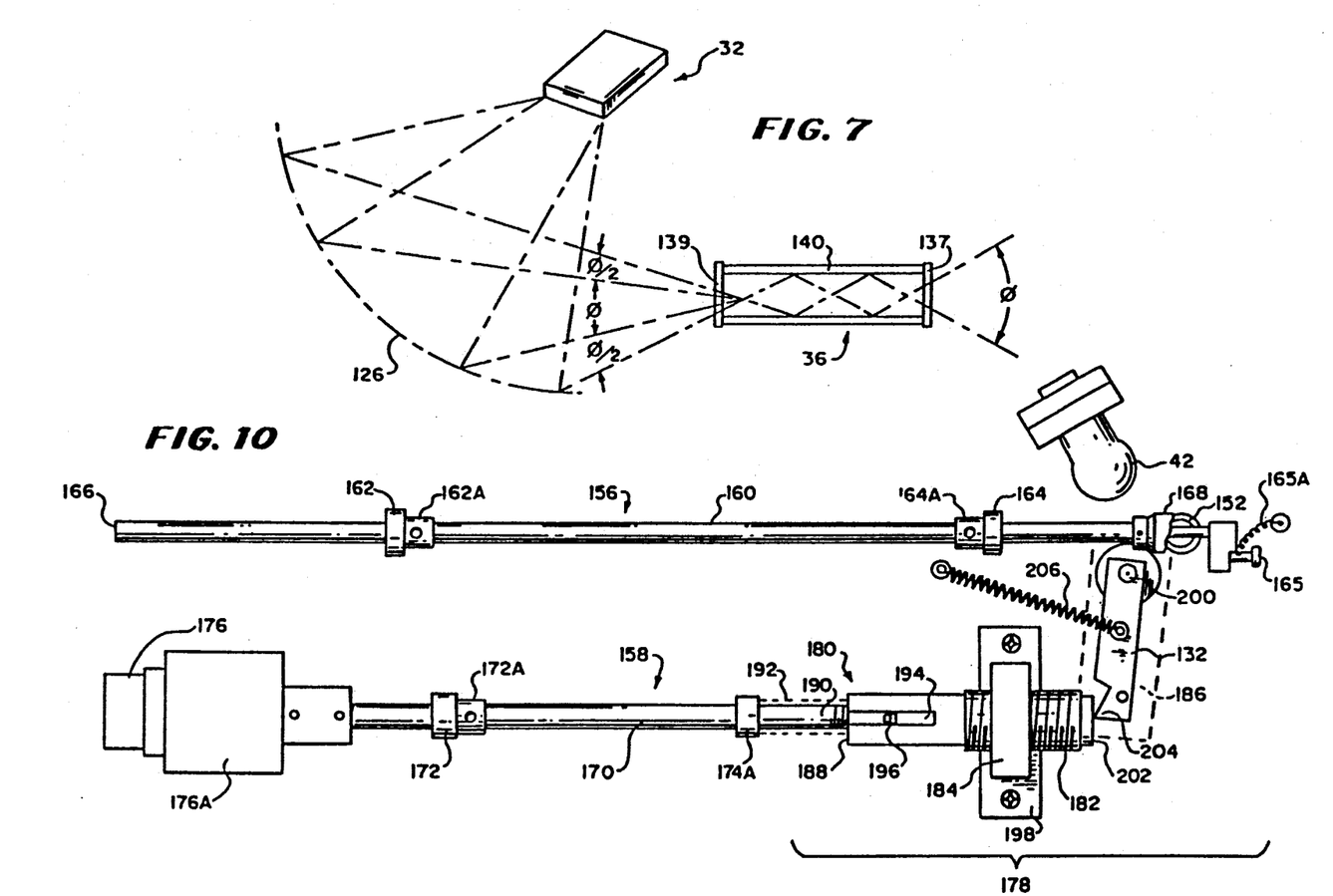
FIG. 7 is a portion of FIG. 2 illustrating the invention in greater detail.
FIG. 10 is a simplified elevational rear view of a portion of the embodiment of FIG. 4.

In FIG. 7 there is shown a schematic view of the flow cell 36, collecting mirror 126 and sensor 32 having light entering the flow cell 36 at an angle $\theta$ and leaving at an angle $\theta + \phi$. The collecting mirror 126 is sufficiently large to collect light leaving at the angle $\theta + \phi$ and focus it onto the light sensor 32.

Light going through the flow cell in the absence of Schlieren scattering enters and leaves the flow cell at the same angle. The reflecting side walls preserve the entrance cone angle $\theta$ and thus light exiting the flow cell, after the multiple reflection, is in a diverging cone of the same angle $\theta$.

Figure 8:
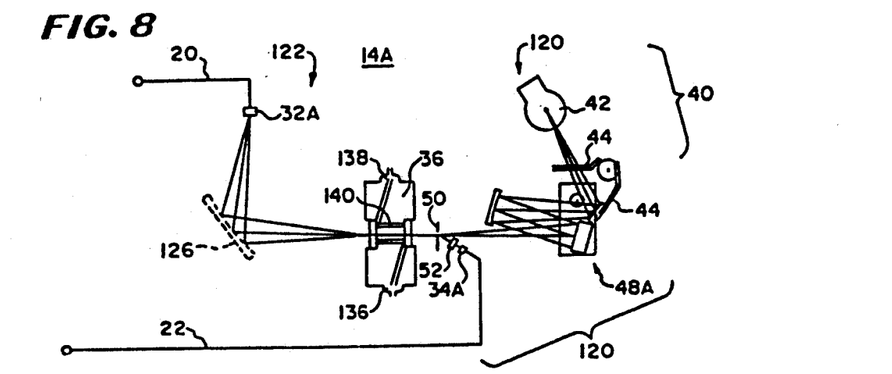
FIG. 8 is another simplified schematic view illustrating the operation of the embodiment of FIG. 4.

The collecting mirror 126 is sufficiently large enough to collect all the light exiting the flow cell in spite of Schlieren scattering increasing the cone by an additional angle $\phi$. The one millimeter inside diameter of reflecting tube 140 forms a one millimeter diameter light entrance at 137 onto which the monochromater is focused. Beam splitter 50 (FIG. 2) partially reflects this same focus onto the one millimeter uniformly sensitive area of reference photosensor 34A (FIGS. 2, 6 and 8).

The images at both the flow cell light path entrance 137 and the light exit 139 of flow cell 36 are one millimeter diameter images of circular cross section which is the same as the original image transmitted throughout the system in the embodiment of FIG. 1. The image at 139 is not a true image as it, point-to-point, is scrambled with respect to 137. However, the light cone angle is preserved and light energy is preserved.

The entrance aperture plate 28A (FIG. 5) and the one millimeter inside diameter of the horizontal sleeve 140 of the flow cell 36 establishes the one millimeter diameter measuring beam and the same aperture plate 28A (FIG. 5) and the one millimeter diameter sensitive area of the reference photocell 34 (FIGS. 2, 6 and 8) establishes the reference beam. These two beams are transmitted to photosensors in a manner similar to that of the embodiment of FIG. 1. The one millimeter (focal diameter) beams are focused onto uniformly sensitive surfaces of photosensors instead of the nonuniform surfaces used in certain embodiments of sensors such as the sensor described in the aforementioned patent application of this continuation-in-part application.

The beam splitter 50 (FIG. 2) is an unsilvered quartz plate which is 0.15 millimeters thick, positioned at an angle similar to that in the embodiment of FIG. 1 to make the amount of plane polarization of the light negligible. The beam splitter is sufficiently thin so that it behaves like a single reflecting surface and there is a negligible double-image effect. As in FIG. 1, the elimination of plane polarization reduces noise because of the difference between the intensity of light along the different axes of the beam of light.

In FIG. 8, there is shown a schematic diagram of the embodiment of FIG. 6 but with the pivotable flat mirror 44 in the incandescent lamp section 40 moved downwardly to block light from the deuterium lamp and to reflect light from the tungsten-krypton lamp 42 into the system in the same manner as in the embodiemnt of FIG. 1. As in the embodiment of FIG. 1, when the mirror 44 is in this position, light is selected between the wavelengths of 350 to 690 nanometers from the tungsten-krypton lamp 42 instead of between 190 and 350 nanometers as in the case when the mirror 44 is raised and light is obtained from the deuterium lamp.

Figure 9:
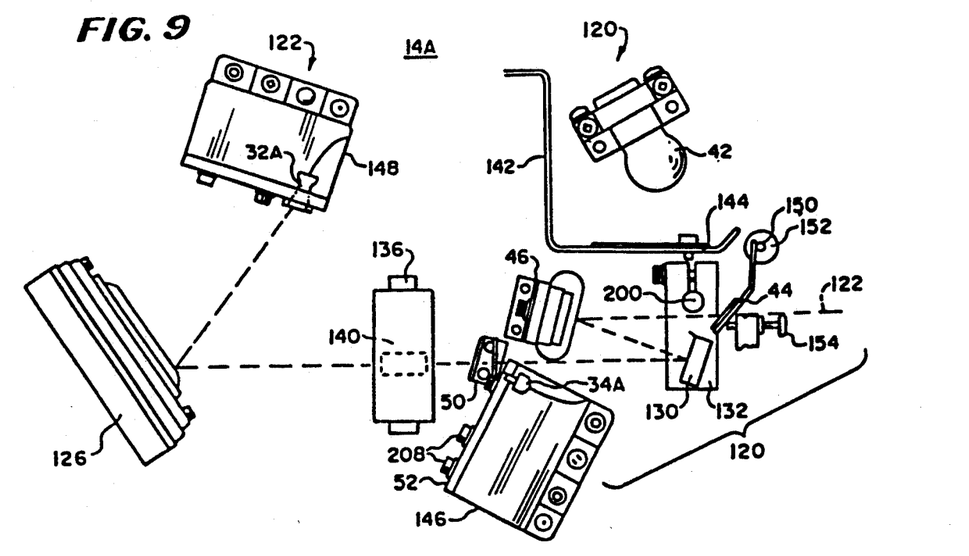
FIG. 9 is a simplified front view of a portion of the embodiment of FIG. 4.

In FIG. 9, there is shown a simplified front elevational view of the optical detecting and electrical sensor station 14A with the pivotable flat mirror 44 positioned to receive light from the tungsten-krypton lamp 42 and direct it into the system. Overlaid upon this is a beam of light 122 as it would pass if the pivotable flat mirror 44 were in its raised position such as that shown in FIG. 6. The pivotable flat mirror 44 is fastened to a shaft 150 for rotation therewith under the control of a bevel gear 152 to move it to and from its opened and closed position. A stop member 154 serves to prevent movement of the pivotable flat mirror 44 beyond a predetermined position aligned to reflect light to the aspheric monochromator focusing mirror 46.

From FIG. 9, it can be understood that light from either the tungsten-krypton lamp 42 or the deuterium lamp 24 (FIG. 5) follows the same course once it is directed onto the aspheric monochromator focusing mirror 46. The difference in light from the two lamps is a differenc of frequency ranges available, and in each case the specific frequency within the range is selected by the diffraction grating lever arm 132.

As best shown in FIG. 9, the light from the tungsten-krypton lamp 42 is shielded from the interior of the optical detecting and electrical sensor station 14A by a box structure 142 and a beam shines through a light filter 129 that passes light in the wavelength range of 350 to 690 nanometers and blocks light of shorter wavelengths that would otherwise pass the grating as an undesired higher diffraction order. Similarly, light from the beam 122 passes beyond (in back of) the diffraction grating lever arm 132 to the aspheric monochromator focusing mirror 46 at an angle unless the pivotable flat mirror 44 is in the position shown in FIG. 9.

Either the beam of light 122 or the light from the tungsten-krypton lamp 42 is reflected by the aspheric monochromator focusing mirror 46 onto the plane reflective diffraction grating 130 which selects a frequency in accordance with the angle of incidence of the light upon it for reflection to the beam splitter 50.

The beam splitter 50 transmits one of two beams through an aperture in a housing 146 against the reference photosensor 34A within the housing 146 which senses it and provides an electrical signal to be used as a reference signal. Another beam is transmitted through the flow cell 136 and is reflected by the aspheric photosensor focusing mirror 126 into the housing 148 which encloses the measuring photosensor 32A.

In FIG. 10, there is shown a simplified elevational rear view of a portion of the embodiment of FIG. 6 having a mirror adjustment assembly 156 and a wavelength adjustment assembly 158 for adjusting the pivotable flat mirror 44 (FIGS. 6, 8 and 9) and the diffraction grating lever arm 132 respectively.

The mirror adjustment assembly 156 includes a shaft 160 rotatably mounted in first and second bearings 162 and 164 respectively. Collars 162A and 164A cooperate with the bearings to prevent excessive end play of shaft 160. One end 166 of the shaft 160 extends outside of the cabinet (not shown) for turning by hand. A bevel gear 168 is rotatably mounted to the shaft near its other end and engages the bevel gear 152 to rotate the pivotable flat mirror 44 about its shaft 150 (FIG. 9). Overcenter arm 165 and spring 165A provide a detent action that holds pivotable flat mirror 44 reproduceably in its position.

With this arrangement, the pivotable flat mirror 44 may be positioned in a closed position where the beam of light 122 (FIG. 9) from the deuterium lamp 24 (FIG. 6) provides a selected frequency of light in the wavelength range between 190 and 350 nanometers and an open position where it reflects light from the tungsten-krypton lamp 42 (FIG. 7) into the system to provide a selected wavelength of between 350 to 690 nanometers to the system.

To select the frequency of light to be used for monitoring a fluid, the wavelength adjustment assembly 158 includes a shaft 170 mounted for rotation in the cabinet by bearing 172 and cam assembly 178. Corresponding shaft collars 172A and 174A cooperate with bearing 172 and cam assembly 178 to prevent end-play of shaft 170.

A wavelength adjustment know 176 is attached to one end of the shaft 170 and a cam assembly 178 is attached to the other so that rotation of the wavelength adjustment knob 176 turns the cam assembly 178. The wavelength adjustment knob 176 extends outside of the cabinet and includes a conventional calibrated multi-turn indication knob with mechanism 176A, the type often used for potentiometer controls (not shown). The cam assembly 178 is designed to provide a linear relationship between the number of degrees of rotation of the wavelength adjustment knob 176 and the wavelength selected by the diffraction grating lever arm 132.

To provide a linear relationship between wavelength and rotation of the wavelength adjustment know 176, the cam assembly 178 includes a coupling assembly 180, a cam 182, a cam nut 184 and a cam follower assembly 186.

The coupling assembly 180 is part of the end of shaft 170 and the end of the cam 182 and includes a cylindrical internal bore 188 within the cylindrical end of the cam 182 facing the shaft 170, a cylindrical portion 190 of the end of the shaft 170 which extends into the cylindrical internal bore 188, a comparatively strong anti-backlash compression spring 192, at least one slot in the walls of the cylindrical internal bore 188 extending outwardly as shown at 194, and a pin extending transverse to the axis of the cylindrical portion 190 of the shaft 170, fastened thereto and extending into the slot 194 as as to turn the cam 182 as the shaft 170 turns.

The cam nut 184 is mounted by a bracket 198 to a frame member and contains a cylindrical tapped bore with double advance internal threads mating with external threads on a cylindrical portion of the cam 182 so that as the shaft 170 turns the cam 182, the cam 182 advances in one direction to the other in alignment with the longitudinal axis of the shaft 170, with the pin 196 moving within the slot 194 to permit longitudinal movement.

To translate the longitudinal movement of the cam 182 to pivoting movement of the diffraction grating lever arm 132, the cam follower assembly 186 is fastened to the diffraction grating lever arm 132 about the pivot point 200 which is the same as the pivot point 200 of the diffraction grating lever arm 132 (FIG. 9). The cam 182 has a cam face 202 against which an end portion 204 of the cam follower assembly 186 rests. A tension spring 206 is mounted to the frame of the instrument housing (not shown) at one end and at the other end to the cam follower asemmbly 186 to hold it against the cam face 202. Spring 206 is much lighter than anti-backlash spring 192.

Before operating the embodiment of FIGS. 4 through FIG. 10, a frequency used for investigation of the components of the fluid passing through the flow cell 136 (FIGS. 6, 8 and 9) is selected.

If the wavelength of the light selected for this purpose is in the range of 350 nanometers to 700 nanometers, the pivotable flat mirror 44 (FIGS. 6, 8 and 9) is lowered by turning the end 166 of the shaft 160 and thus rotating the bevel gears 168 and 152 (FIG. 10) until the pivotable flat mirror 44 is in the position shown in FIG. 9. In this position it receives light from the tungsten-krypton lamp 42 and transmits it to the aspheric monochromator focusing mirror 46. If the wavelength is in the range of 190 to 350 nanometers, then the pivotable flat mirror 44 is raised instead of lowered so that light from the deuterium lamp 24 (FIG. 5) is transmitted through the slot 124 of the aperture plate 28A into the transverse axis and frequency adjustment assembly 120 (FIGS. 6, 8 and 9).

To provide the selected wavelength of light, the diffraction grating lever arm 132 (FIGS. 6 through 10) must also be adjusted to the selected frequency. This is accomplished by turning the wavelength adjustment knob 176 (FIG. 10) to the frequency which is shown on a scale (not shown) adjacent to the wavelength adjustment knob 176. As the knob is turned, the shaft 170 turns and rotates the cam 182 to cause the cam follower assembly 186 to rise or fall on the cam face 202 and thus pivot the diffraction grating lever arm 132 about the pivot point 200. This adjustment is made until the plane reflective diffraction grating 130 is at the proper angle to the light for the selected frequency.

After the frequency has been selected, fluid is passed through the flow cell entering at the entrance 136 and flowing upwardly through the horizontal sleeve 140 (FIGS. 6 and 8).

While the fluid to be investigated is flowing, light from the tungsten-krypton lamp 42 or from the light source 12A (FIG. 4): (1) enters the system; (2) is reflected by the aspheric monochromator focusing mirror 46 onto the plane reflective diffraction grating 130; and (3) a selected frequency is reflected from there to the beam splitter 50. One beam from the beam splitter 50 is transmitted through the flow cell at 140 against the aspheric photocell focusing mirror 126 and from there to the silicon diode measuring photosensor 32A. Another beam is transmitted through a hole in the housing 146 and onto the photosensor surface of reference photosensor 32A which has the same diameter as the horizontal sleeve 140 and is adjusted in position for low noise.

As in the embodiment of FIG. 1, the aperture for the horizontal sleeve 140 and the circular-shaped photosensitive surface of silicon diode reference photosensor 34A mounted to the housing 146 are one millimeter in diameter. The photosensor in the housing 146 is adjusted by adjusting the mounting plate 42 which is mounted to the housing 146 by fasteners 208. This adjustment is made to remove noise by causing the same portion of the light beam to reach the reference photosensor 34A as it passes through the cylindrical one miilimeter diameter horizontal sleeve 140. That horizontal sleeve 140 is internally coated with a reflective material to prevent loss of light and thus reduce noise.

When the beam of light 122 from the deuterium lamp is used, the adjustment of the positions of the diffraction grating lever arm 132 selects the angle at which the light from the aspheric monochromator focusing mirror 46 impinges upon the plane reflective diffraction grating 130 and thus the frequency of light. The beam of light 122 is from the slot 124, selected to have virtually no noise in its narrow width and a greater length than necessary along the length of the slot, the length being increased at the expense of more noise at its extremeties for a special purpose.

In the preferred embodiment, this slot has a height of 0.6 millimeters and a width of 2 millimeters. The aspheric condensing mirror 26 focuses light from a correspondingly sized slot at the center of the center bright spot of the deuterium lamp 24 through the slot 124 to provide a minimum-noise beam which is determined by the rectangular aspheric monochromator focusing mirror 46 to form a rectangular cross-section beam and from thence upon the rectangular diffraction grating 130.

The slot-cross-section beam of light from the deuterium lamp 24 diverges to the aspheric condensing mirror 26 which causes it to converge to the slot 124 of the aperture plate 28A (FIG. 5). From thence it diverges to the aspheric monochromator focusing mirror 46 (FIGS. 6–9) which focuses it in a converging beam to the plane reflective diffraction grating 130 which reflects it to the beam splitter 50.

As the frequency is selected by pivoting the diffraction grating lever arm 132, the focal point of the frequency to be used in investigating the fluid changes because the frequency is changed. However, since the plane reflective diffraction grating 130 orbits about a specially selected pivot point 200, the light waves having one axis remain in focus with the one millimeter horizontal sleeve 140 in the flow cell 36 (FIG. 9). A portion of the focal point of light waves aligned with a transverse axis also is focused on the one millimeter sleeve but the portion of the light passing through the slot 124 that is formed moves in a plane transverse to the cross section of the beam. This shift occurs because there is a known relationship in the shifting of the focus between light waves of the two axes.

The shift in the axis parallel to the slot is relatively small and there is nonetheless a substantial portion slightly less than one millimeter which is in focus with the horizontal sleeve 140 while the portions of light having the same axis will not pass through the horizontal sleeve 140, thus resulting in a less noisy beam exiting from the flow cell 36. Similarly, the other beam from the beam splitter 50 is focused and preferentially the light in focus along one axis is focused on the one millimeter diameter photosensitive surface photosensor 34A.

Because the silicon photosensors have uniform sensitivity over their entire surface, shifts in the positions of the light with respect to the surface of the photosensors caused by shifts in the location and angle of emission in the deuterium lamp do not affect the resulting electrical signal. Consequently, the signals from the optical detecting and electrical sensor station 14A through conductors 20 and 22 (FIG. 4) are of lower noise in the embodiment of FIG. 4 than that of FIG. 1.

As can be understood from the above description, the embodiment of this invention has the advantages of achieving low noise without excessively expensive diffraction gratings, mirrors, or focusing systems.

Although a specific embodiment of the invention has been described with some particularity, many modifications and variations in the embodiment are possible without deviating from the invention. Therefore, it is to be understood that, within the scope of the appended claims, the invention may be practiced other than as specifically described.

What is claimed is:

1. A method of determining the absorbance of a liquid flowing through an absorbance monitor having a gas discharge lamp as a light source, a diffraction grating for selecting certain frequencies of light, a reference photocell, a measuring photocell, a beam splitter for developing a measuring beam of light and a reference beam of light from light emitted by the gas discharge lamp, a flow cell having a liquid channel and a light channel which intersect each other and a comparator, which process comprises the steps of: transmitting the measuring beam of light through the light channel of the flow cell to the measuring photocell; transmitting the reference beam of light to the reference photocell, whereby reference and measuring signals are generated by the reference and measuring photocells respectively; and comparing said reference and measuring signals, wherein the improvement comprises:

obtaining one selected frequency of light flux from a predetermined area of the gas discharge lamp without significant polarization and with waves aligned with sagital plane focused and waves aligned with the tangential plane focused on the same point;

transmitting the one selected frequency of light flux from the predetermined area into intimate contact with a sample without significant plane polarization; and transmitting the one selected frequency of light flux onto a photosensor of a type having a small sensing area of substantially uniform sensitivity;

the step of transmitting the one selected frequency of light flux including the substep of transmitting the one selected frequency of light flux through a flow cell having a reflecting tube in the flow cell with an oval cross-section aligned with an oval light spot from the light source.

* * * * *